United States Patent
de Potzolli et al.

(10) Patent No.: US 11,737,961 B2
(45) Date of Patent: Aug. 29, 2023

(54) PRESERVATION MIXTURES, AND POLYMER SOLUTIONS STABILIZED THEREWITH

(71) Applicant: BASF SE, Ludwigshafen (DE)

(72) Inventors: Bernd de Potzolli, Bad Duerkheim (DE); Monika Rausch, Dannstadt-Schauernheim (DE); Karin Juhkason, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 799 days.

(21) Appl. No.: 15/126,706

(22) PCT Filed: Mar. 13, 2015

(86) PCT No.: PCT/EP2015/055291
§ 371 (c)(1),
(2) Date: Sep. 16, 2016

(87) PCT Pub. No.: WO2015/144458
PCT Pub. Date: Oct. 1, 2015

(65) Prior Publication Data
US 2017/0087070 A1 Mar. 30, 2017

(30) Foreign Application Priority Data

Mar. 25, 2014 (EP) .................... 14161479

(51) Int. Cl.
| | | |
|---|---|---|
| *A61K 8/34* | (2006.01) | |
| *A61Q 5/00* | (2006.01) | |
| *A61Q 5/06* | (2006.01) | |
| *A61Q 5/02* | (2006.01) | |
| *A61Q 19/00* | (2006.01) | |
| *A61Q 19/10* | (2006.01) | |

(52) U.S. Cl.
CPC ............... *A61K 8/345* (2013.01); *A61K 8/34* (2013.01); *A61Q 5/00* (2013.01); *A61Q 5/02* (2013.01); *A61Q 5/06* (2013.01); *A61Q 19/00* (2013.01); *A61Q 19/10* (2013.01); *A61K 2800/30* (2013.01); *A61K 2800/524* (2013.01)

(58) Field of Classification Search
CPC ...... A61K 8/345; A61K 8/34; A61K 2800/30; A61K 2800/524; A61K 8/8176; A61K 8/8182; A61K 8/87; A61Q 5/02; A61Q 5/00; A61Q 5/06; A61Q 19/00; A61Q 19/10; A61Q 5/12
See application file for complete search history.

(56) References Cited

U.S. PATENT DOCUMENTS

| | | | |
|---|---|---|---|
| 5,670,160 A | 9/1997 | Eggensperger et al. | |
| 2005/0154067 A1* | 7/2005 | Beilfuss | A01N 31/02 514/715 |
| 2005/0228032 A1 | 10/2005 | Merianos et al. | |
| 2007/0081964 A1* | 4/2007 | Muller | A61K 8/817 424/70.15 |
| 2009/0175806 A1* | 7/2009 | Modak | A61K 8/365 424/58 |
| 2011/0152383 A1* | 6/2011 | Schmaus | A01N 31/02 514/731 |
| 2013/0068849 A1* | 3/2013 | Birkel | A61Q 5/06 239/1 |
| 2013/0136709 A1 | 5/2013 | Pillai et al. | |

FOREIGN PATENT DOCUMENTS

| | | | | |
|---|---|---|---|---|
| CN | 103083196 A | 5/2013 | | |
| DE | 40 26 756 A1 | 2/1992 | | |
| JP | H1053510 A | 2/1998 | | |
| WO | WO-2007071089 A1 * | 6/2007 | ............... | A61K 8/33 |
| WO | WO-2008/071027 A1 | 6/2008 | | |
| WO | WO-2014/032989 A1 | 3/2014 | | |

OTHER PUBLICATIONS

Database GNPD [Online] Mintel; Feb. 28, 2014 (Feb. 28, 2014), "Eye Cream," XP002726539, Database accession No. 2265088 abstract.
International Search Report in international patent application No. PCT/EP2015/055291, dated Jun. 15, 2015.

* cited by examiner

*Primary Examiner* — Abigail Vanhorn
(74) *Attorney, Agent, or Firm* — MARSHALL, GERSTEIN & BORUN LLP

(57) ABSTRACT

The present invention describes specific biocidally effective preservative mixtures and aqueous polymer solutions stabilized with these preservative mixtures and their use in cosmetic preparations, such as skin care and hair care compositions, and hairstyling products and in products for the home care sector.

9 Claims, No Drawings

PRESERVATION MIXTURES, AND POLYMER SOLUTIONS STABILIZED THEREWITH

CROSS-REFERENCE TO RELATED APPLICATIONS

This is the U.S. national phase of International Application No. PCT/EP2015/055291, filed Mar. 13, 2015, which claims the benefit of European Patent Application No. 14161479.2, filed Mar. 25, 2014.

The present invention relates to specific biocidally effective preservative mixtures and to aqueous polymer solutions which have been stabilized with these preservative mixtures or by mixing in said biocidally effective individual components and to their use in cosmetic preparations, such as skin care and hair care compositions, and hairstyling products and in products for the home care sector.

The growth of microorganisms such as bacteria and viruses and also fungi and yeasts in polymer solutions, in particular aqueous polymer solutions, is to be avoided in many respects. Microorganisms in aqueous polymer solutions lead to an unhealthy buildup of germs and therefore constitute a high hygiene risk, especially if the polymer solutions are incorporated into cosmetic products, for example as binders, thickeners or film formers.

It is known to stabilize aqueous polymer solutions with biocides or antimicrobial compounds as preservatives to combat troublesome buildups of germs. They are incorporated into the polymer solution as additives. However, it has been found that some of the known preservatives are carcinogenic or sensitizing and are not suitable for use in cosmetic preparations. For example, it has been known for some time that 2-methyl-isothiazolin-3-one (MIT), a very often used preservative of aqueous polymer solutions, is sensitizing and therefore harmful to health.

Disadvantages of alternative additives which are approved worldwide are that a lack of product stability is to be noted. The result is therefore very often discolorations, clouding, phase separations, adverse changes in odor and inadequate microbiological effectiveness in the polymer solutions to which they are added.

It is therefore an object of the present invention to avoid undesired buildups of germs in aqueous polymer solutions while retaining good product stabilities. It is furthermore an object of the present invention to develop a technology with which cosmetic products can be produced without concern as regards their ingredients.

These objects have been achieved with the present invention.

The present invention relates to aqueous MIT-free polymer solutions stabilized with a preservative mixture of phenoxyethanol and at least one further alcohol.

The present invention likewise provides the polymers present/obtained in/from the stabilized aqueous polymer solutions.

The invention further relates to the use of the aqueous polymer solution in cosmetic preparations, such as skincare and hair care compositions, hairstyling products, products of decorative cosmetics and cosmetic cleaning, e.g. shampoos and shower gels, and also liquid soaps.

Moreover, the invention relates to MIT-free preservative mixtures for stabilizing aqueous polymer solutions.

The dependent claims relate to preferred embodiments of the aqueous polymer solution according to the invention, to its polymers, and to the use.

The amounts for the constituents of the preservative mixture refer to 100% by weight of aqueous polymer solution.

The aqueous polymer solution according to the invention comprises a preservative mixture which has, in a balanced low dosage, phenoxyethanol and at least one further alcohol as biocidally effective active ingredients. These specific preservative mixtures are free from 2-methylisothiazolin-3-one (MIT), a preservative that has been shown to be harmful to health. Furthermore, the preservative mixtures comprise no paraben or polyaminopropylbiguanide.

It had been established that aqueous polymer solutions which comprise only one constituent of the preservative mixture, i.e. only phenoxyethanol or an alcohol, do not exhibit an adequate stabilizing effect even in a much higher concentration. It was therefore all the more surprising that the preservative mixtures with phenoxyethanol in combination with an alcohol in a low concentration range of the individual components exhibit unexpected effects in connection with the microbial stabilization of the aqueous polymer solutions according to the invention. It has furthermore proven to be particularly advantageous that the polymer solutions comprising the preservatives according to the invention are stable, clear, colorless, color-stable and odor-acceptable (no troublesome foreign odors) and do not exhibit phase separation. Moreover, in the case of the various applications, no disadvantages such as e.g. clouding and discolorations and no lowering of the viscosities in the case of, for example, gels and foams etc. are to be noted.

A further advantage of the present invention is considered to be that the polymer solutions according to the invention can be stabilized by the low concentration of the preservatives in an extremely economical manner in the sense of cost-effectiveness.

The synergistically intensifying effectiveness of the phenoxyethanol with at least one further alcohol as booster is directed against various germs or germ mixtures, such as, for example, Gram-positive and Gram-negative bacteria, yeasts and molds. In this connection, the product stability of the aqueous polymer solutions according to the invention is retained. The booster effect can, however, also start from the phenoxyethanol. This result was unforeseeable, particularly with regard to the fact that the individual components in the preservative mixture are present in substantially lower concentrations in the polymer solutions compared to conventional preservatives. In a preferred embodiment of the present invention, the alcohols of the preservative mixture are selected from the group of mono-, di- and trivalent alcohols, and mixtures thereof. Preference is given here to aliphatic and aromatic alcohols, where the aliphatic chains may be straight-chain or branched-chain.

Particularly preferred aqueous polymer solutions are those stabilized with preservative mixtures which, besides phenoxyethanol, comprise alcohols from the group ethylhexylglyceryl, 1,3-propanediol, 1,2-pentanediol, 1,2-octanediol, 3-phenylpropanol, 2-phenylethanol, ethanol, isopropanol and 1,2-decanediol, and mixtures thereof. Very particular preference is given to 3-phenylpropanol, 1,3-propanediol, 1,2-pentanediol, 1,2-octanediol, 1,2-decanediol, ethanol, isopropanol and mixtures thereof.

The concentration of the preservative mixture in the aqueous polymer solution is in a range from 0.05 to 1.40% by weight, preferably in a range from 0.10 to 0.65% by weight and very particularly preferably in a range from 0.10 to 0.40% by weight.

The present invention likewise describes preservative mixtures which are used for the stabilization of aqueous polymer solutions.

A preservative mixture according to the invention (mixture A) has the following constituents as biocidally effective active ingredients:
25 to 50% by weight of a mixture of 50% 3-phenylpropanol, 25% 1,3-propanediol and 25% 1,2-octanediol and
50 to 75% by weight phenoxyethanol,
based on 100% by weight of mixture.

A further preservative mixture according to the invention (mixture B) has the following composition:
20 to 57% by weight of a mixture of 50% 1,2-pentanediol, 30% 1,2-octanediol and 20% 1,2-decanediol and
43 to 80% by weight of phenoxyethanol
based on 100% by weight of mixture.

The aqueous polymer solution of the present invention is microbially stabilized by the specific preservative mixtures or by adding the individual components. In order to achieve the claimed concentration range in the aqueous polymer solution, the mixture A is used in an amount of from 0.10 to 1.40% by weight. The mixture A is used in an amount of from 0.2 to 0.8% by weight in order to obtain a preferred aqueous polymer solution. The mixture A is used in an amount of from 0.40 to 0.60% by weight in order to prepare a very preferred aqueous polymer solution. The mixture B is used in an amount of 0.20-1.4% by weight. A preferred range is 0.25 to 0.75 by weight in the solution, where 0.30 to 0.60% by weight is particularly preferred.

The term "polymer" comprises for example linear, water-soluble branched or water-insoluble linear and branched polymers. The term "water-insoluble branched polymer" also comprises the so-called popcorn polymers, which are referred to as "proliferous polymers" or as in the case of polyvinyl pyrrolidone as PVPP.

Within the context of this invention, "branched", "branching", "crosslinked", "crosslinking" are used interchangeably to mean a polymer which has at least one branching site.

"Polymer" also comprises the copolymers, graft homopolymers or graft copolymers, which can in each case be present as linear or soluble-crosslinked, in particular water-soluble-crosslinked, or insoluble-crosslinked, in particular water-insoluble-crosslinked, polymers.

"Polymer" can be present in any form, for example as di- or multi-block polymers, and also be present in star form, brush form or hyperbranched form or as dendrimer.

Polymers according to the invention comprise one or more monomers a), optionally one or more monomers b), and optionally one or more crosslinking monomers c), i.e. they have been obtained by polymerization of the specified monomers and can also comprise residual amounts of the monomers.

Monomers a) are selected from:
N-Vinyllactams such as N-vinylpyrrolidone, N-vinylpiperidone, N-vinylcaprolactam, derivatives thereof substituted with C1 to C8-alkyl groups such as 3-methyl-, 4-methyl- or 5-methyl-N-vinylpyrrolidone and mixtures thereof, vinyl acetate and mixtures of N-vinyllactams, preferably with N-vinylpyrrolidone, vinyl acetate and also acylates and methacylates including acids thereof and monomer mixtures thereof with N-vinyllactams and/or vinylimidazoles and/or quaternized vinylimidazoles, and also diisocyanates and diamines for the formation of polyurethanes with or without terminal EO/PO fatty alcohols, N-vinylamides such as N-vinylformamide and its N-vinylamine obtainable after the polymerization by hydrolysis, N-vinyl-N-methylacetamide.

Amines such as N-vinyl- or allyl-substituted heterocyclic compounds, preferably N-vinylpyridine, or N-allylpyridine, N-vinylimidazoles, which can also be substituted in the 2, 4 or 5 position with C1-C4-alkyl, in particular methyl or phenyl radicals, such as 1-vinylimidazole, 1-vinyl-2-methyl (ethyl)vinylimidazole, and quaternized analogs thereof such as 3-methyl-1-vinylimidazolium chloride, 3-methyl-1-vinylimidazolium methyl(ethyl)sulfate, N—C1- to C24-alkyl-substituted diallylamines or quaternized analogs thereof such as diallylammonium chloride or diallyldimethylammonium chloride and diamines.

Here, polymers according to the invention preferably comprise at least one N-vinyllactam monomer.

Further monomers a) can be polyacrylamides, polymethacrylamides, polyacrylates, polymethacrylates, neutral polyacrylic acids, and neutral polymethacrylic acids.

Polymers according to the invention can be homopolymers or copolymers of two or more monomers a), for example copolymers of N-vinylpyrrolidone and N-vinylimidazole, copolymers of N-vinylpyrrolidone and N-vinylformamide, copolymers of N-vinylpyrrolidone and N-vinylcaprolactam, copolymers of N-vinylpyrrolidone, N-vinylcaprolactam and N-vinylimidazole or copolymers of N-vinylpyrrolidone and N-vinylimidazole and quaternized N-vinylimidazoles.

Preferred monomers a) are vinyllactams such as N-vinylpyrrolidone, 3-methyl-N-vinylpyrrolidone, 4-methyl-N-vinylpyrrolidone, 5-methyl-N-vinylpyrrolidone, N-vinylpiperidone and N-vinylcaprolactam, vinyl acetate, and the vinyl alcohol obtainable after the polymerization by hydrolysis, vinylamides such as vinylformamide, and the vinylamine obtainable by hydrolysis after the polymerization, N-vinylimidazole, 1-vinyl-3-methylimidazolium chloride, 1-vinyl-3-methylimidazolium sulfate, and vinylmethylamide, and derivatives thereof.

Further preferred monomers a) are acylates and methacylates and their acids, and also diamines.

Very particularly preferred monomers a) are N-vinylpyrrolidone, N-vinylcaprolactam, vinyl acetate, vinylformamide, and also the vinylamine obtainable by hydrolysis after the polymerization, and also N-vinylimidazole.

Suitable monomers b) are all monomers which are specified in WO 2010/072640 A1 as "monomer b)" on page 6, from line 8, to page 8, line 17, to which reference is made here in its entirety.

Preferred monomers b) are acrylates, acrylic acid, alkylacrylates, alkylacrylic acids, methacrylates, methacrylic acid, alkyl methacrylates, alkylmethacrylic acids, maleic acid, maleic anhydride, isopropylmethacrylamide, acrylamide, methacrylamide, 2-hydroxyethyl-acrylamide and 2-hydroxyethylmethacrylamide, also vinyl esters of aliphatic C2-C18-carboxylic acids such as vinyl acetate, and also the vinyl alcohol obtainable by hydrolysis after the polymerization, vinyl propionate, vinyl butyrate, vinyl laurate, vinyl stearate, vinyl neodecanoate VEOVA 9 and VEOVA 10, also dimethylaminoethyl (meth)acrylate and dimethylaminoethyl (meth)acrylamide and quaternized analogs thereof, and also diallyldimethylammonium chloride and diisocyanates, and also styrene and styrene derivatives.

Very particularly preferred monomers b) are methacrylamide, vinyl acetate, and the vinyl alcohol obtainable by hydrolysis after the polymerization, vinyl propionate, vinyl neodecanoate VEOVA 9 and VEOVA 10, dimethylaminoethyl (meth)acrylate or dimethyl-aminoethyl(meth)acrylamide or quaternized analogs thereof, and also diallyldimethylammonium chloride.

Polymers which are copolymers and comprise monomers b) can comprise one or more of the monomers b). Usually, however, not more than five different monomers b) are present in one copolymer.

The preferred polymers further include copolymers which comprise one or more monomers a) and/or one or more monomers b).

Suitable crosslinking monomers c) ("crosslinkers") are: crosslinking monomers c) are described for example in WO2009/024457 on page 7, line 1 to page 9, line 2, to which reference is expressly made here.

Particularly preferred crosslinking monomers c) are pentaerythritol triallyl ether, methylene-bisacrylamide, N,N'-divinylethyleneurea, divinylbenzene, ethylenebis-N-vinylpyrrolidone, 3-vinyl-N-vinylpyrrolidone, 4-vinyl-N-vinylpyrrolidone, 5-vinyl-N-vinyl pyrrolidone, allyl (meth) acrylate, triallylamine and acrylic acid esters of glycol, butanediol, trimethylolpropane or glycerol, and also acrylic acid esters of glycol, butanediol, trimethylolpropane or glycerol reacted with ethylene oxide and/or epichlorohydrin.

The quantitative fractions in percent by weight based on the total mass of the polymer here are, for the monomers a), usually at least 20, preferably at least 30, particularly preferably at least 50, especially preferably at least 60 percent by weight and very particularly preferably up to 100 percent by weight, such as, for example, homopolymers of 100% of a monomer a).

The quantitative fractions in percent by weight, based on the total mass of the polymer, here are, for the monomers b), usually up to 80, preferably up to 70, particularly preferably up to 50, especially preferably up to 40 and very particularly preferably less than 5 percent by weight and are for example not present at all in the polymer.

If the polymer is water-soluble crosslinked polymer, the quantitative fractions of the crosslinking monomers c) in percent by weight, based on the total mass of the polymer, are usually 0.001 to 20, preferably 0.01 to 10, particularly preferably 0.05 to 5 and in particular 0.1 to 1 percent by weight.

If the polymer is water-insoluble crosslinked polymer such as, for example, a popcorn polymer, the quantitative fractions of the crosslinking monomers c) in percent by weight, based on the total mass of the polymer, are usually 0.001 to 10, preferably 0.01 to 5, particularly preferably 0.1 to 3 and especially 0.5 to 2 percent by weight.

If crosslinking monomer c) is used, then the overall quantitative fractions of monomer a) and optionally monomer b) are reduced correspondingly by the amount of crosslinking monomer c) used.

The monomers a), b) and c) used for the polymerization can, independently of one another, be an individual or mixtures of two or more monomers a), monomers b) and/or monomers c), where the combined quantitative fraction of the monomers a), b) or c) gives the quantitative fraction specified in each case therefor for monomer a), for monomer b) or for monomer c) based on the polymer.

The total amounts of monomer(s) a) plus monomer(s) b) plus monomer(s) c) always add up here to 100 percent by weight.

A vinyllactam polymer can be a homopolymer or copolymer comprising N-vinyllactams such as N-vinylpyrrolidone (VP) or 3, 4- or 5-position methyl-substituted derivatives thereof, N-vinylpiperidone or N-vinylcaprolactam (VCap). Preference is given to N-vinylpyrrolidone, N-vinylcaprolactam or mixtures thereof. N-Vinylpyrrolidone is especially preferred.

Preferred vinyllactam polymers are vinylpyrrolidone polymers such as polyvinylpyrrolidones, vinylpyrrolidone copolymers and vinylpyrrolidone popcorn polymers.

Preferred polyvinylpyrrolidones are polymers with K values of 1 to 150, preferably K10 to K120, for example K12, K15, K17, K25, K30, K60, K85, K90, K95, K100, K115 or K120. Particularly preferred PVP homopolymers have a K value of 12 to 95 and especially preferably of 30 to 90, such as in particular K30, K60, K85 and K90.

Preferred vinylpyrrolidone copolymers are linear, uncrosslinked copolymers with N-vinylcaprolactam (VCap), vinyl acetate (VAc), N-vinylimidazole (VI), quaternized N-vinylimidazole and/or derivatives thereof and/or mixtures thereof.

Particularly preferred copolymers are copolymers of N-vinylpyrrolidone (VP) with vinyl acetate with a weight ratio VP/VAc of 20:80 to 80:20, for example 30:70, 50:50, 60:40, 70:30, with K values of 10 to 90, preferably of 15 to 80 and in particular of 20 to 60. Very particularly preferred copolymers of N-vinylpyrrolidone with vinyl acetate have a K value of 22 to 40 and a weight ratio VP to VAc of 50:50 to 70:30.

Preference is likewise given to copolymers of VP and VCap with K values of 10 to 100, preferably of 12 to 80 and in particular of 20 to 75, and also weight ratios of the monomers VP to VCap from 80:20 to 20:80, preferably from 70:30 to 30:70, especially preferably from 60:40 to 40:60 and for example also 50:50.

The K value of the vinylpyrrolidone copolymers and of the polyvinylpyrrolidones (Fikentscher K value; see for example Bühler, "Polyvinylpyrrolidone—Excipient for Pharmaceuticals", Springer, 2005, pages 40 to 41) is a measure of the solution viscosity at defined conditions. Consequently, it is a direct measure of the molar mass. If the molar mass changes, for example as a result of oxidative processes, this leads to an increase in molar mass (leads to an increase in K value) or to a reduction in molar mass (leads to a reduction in K value) and thus to a change in the K value. If the molar mass changes, then the solution viscosity of a solution with a defined solids content also changes accordingly.

Preferred aqueous polymer solutions are polyvinylpyrrolidone solutions, polyvinylpyrrolidone/polyvinyl acetate solutions, PVP/(VCap)/VI, quart. QVI solutions and polyurethane solutions.

The aqueous polymer solutions are prepared by conventional processes, for example by stirring in the preservative mixtures according to the invention or by directly mixing in the individual components of the at least two preservatives/boosters.

The stabilized polymers of the invention are prepared from the aqueous solutions in a customary manner, for example by drying, such as spray drying, drying on contact surfaces and drying by means of vacuum.

According to the invention, the aqueous polymer solutions stabilized with the preservative mixture and the polymers thereof are used in cosmetic preparations as, for example, binders, thickeners or film formers. Examples of such cosmetic preparations are skincare and hair care compositions. The skincare compositions include, for example, creams, gels, gel creams, waxes, wax gels, gel waxes and lotions. The hair care compositions include, for example, creams, gels, gel creams, waxes, wax gels, gel waxes, styling and conditioning foams, and also spays (pump sprays and aerosol sprays) and lotions. In this connection, mention is also to be made of products for cosmetic cleaning, which include shower gels and bath gels.

The aqueous polymer solutions stabilized with the preservative mixtures according to the invention are also used successfully in the home care sector. They are therefore suitable for incorporation into domestic cleaners, for example for hard surfaces.

The stabilized aqueous polymer solutions according to the invention and the polymers therefrom can likewise be used in decorative cosmetics. These include, for example, make-ups, lipsticks, concealers and mascaras.

A cosmetic preparation is usually in the form of a gel, wax, wax gel, gel wax, foam, spray or emulsion or dispersion and can comprise a number of further cosmetic additives. Depending on the use of the preparation according to the invention, further additives also have to be admixed; these are selected from the group which is formed from emulsifiers, surfactants, pearlescent waxes, stabilizers, salt, thickeners, consistency regulators, inorganic and organic UV photoprotective filters, self-tanning agents, pigments, antioxidants, hydrotopes, biogenic active ingredients, dyes, customary preservatives, preferably benzoic acid or citric acid, humectants such as glycerol, ethanol, propylene glycol, antidandruff agents, swelling agents and perfumes. Preferred biogenic active ingredients here are in particular tocopherol, tocopherol acetate, tocopherol palmitate, deoxyribonucleic acid, coenzyme Q10, ascorbic acid, retinol and retinyl derivatives, bisabolol, allantoin, phytantriol, panthenol, AHA acids, amino acids, ceramides, essential oils, hyaloronic acid, creatine, protein hydrolysates, plant extracts, peptides and vitamin complexes.

A further aspect of the present invention lies in the use of the aqueous polymer solution stabilized according to the invention or of the polymers thereof as conditioning agents in hair care compositions. The aqueous solution stabilized according to the invention and the polymers thereof can be incorporated into hair shampoos, hair care compositions, hair lotions, hair treatments, hair gel, hair mousses, conditioners, hair tonics and hairstyling products, such as styling and conditioning mousses, hair gels, hair mousses, hair-setting compositions (in e.g. sprays and lotions) and hair waxes. The use in hair shampoo necessitates the use of further surfactants and also auxiliaries and additives. The addition of further customary additives depends on the particular product.

On account of its biocidal properties and its use in extremely low concentrations, the preservative mixture according to the invention is exceptionally suitable for stabilizing aqueous polymer solutions. The product stability of the stabilized polymer solutions is retained over a long period, the appearance and the sensory properties are unchanged and there are no color changes or clouding, nor phase separation of the solutions. The polymer solutions according to the invention and also the polymers thereof exhibit an extraordinarily good microbial stability and can be incorporated without concern into cosmetic products and hair care compositions and also hairstyling products.

The invention is illustrated by reference to the following examples.

EXAMPLES

To ascertain the freedom from germs of the aqueous polymer solutions, germ loading tests were carried out which satisfy the requirements of the pharmacopeia for topical applications (e.g. PhEur., USP and JP). Furthermore, the "Koko test" was carried out which, compared to PhEur., provides up to six-fold inoculations with germs.

The passed germ loading test according to Ph. Eur., 7th Edition with the stabilized aqueous polymer solutions exhibited after 28 days freedom from germs with regard to the tested strains *Pseudomonas aeruginosa* (ATCC 9027), *Staphylococcus aureus* (ATCC 6638), *Candida albicans* (ATCC 10231) and *Aspergillus brasiliensis* (ATCC 16404).

Table 1 below shows by way of examples 1 to 18 polymer solutions according to the invention stabilized with various preservative mixtures in different concentrations. As can be seen, all of the stabilized polymer solutions pass the germ loading test. The polymer solutions of examples 1 to 15 comprise the preservative mixture in a very low concentration in the range from 0.4 to 0.8% by weight, the products being clear and not very odor-intensive. No phase separations are noted. It is noteworthy that the aqueous Luviskol K85/90 solutions with ethanol or isopropanol of examples 16 to 18 in combination with relatively high fractions of phenoxyethanol in a concentration in the range from 0.85 to 1.35% by weight can be effectively stabilized. Here, the boosting effect of ethanol or isopropanol on the phenoxyethanol is clear to see.

The preservative used as a) comprises phenoxyethanol as individual component.

The preservative mixture used as b) comprises the individual components in the following fractions:
42 to 48% phenylpropanol, 23 to 27% 1,2-octanediol and 27 to 33% 1,3-propanediol.

The preservative mixture c) comprises the individual components as follows:
25 to 50% 1,2-pentanediol, 25 to 50% 1,2-octanediol and 10 to 25% 1,2-decanediol.

The preservative mixture d) comprises 90% phenoxyethanol and 10% ethylhexylglyceryl.

The preservative e) is either ethanol or isopropanol.

TABLE 1

| Example | Polymer in aqueous polymer solution | Preservative mixture | Concentration of the individual components in the polymer solution (% by weight) | Germ loading test | Appearance of the stabilized solution |
|---|---|---|---|---|---|
| 1 | Luviset Clear * | a) 2-Phenoxyethanol<br>b) Phenylpropanol<br>   1,2-Octanediol<br>   1,3-Propanediol | a) 0.10<br>b) 0.30 | Passed | Almost clear |
| 2 | Luviset Clear * | a) 2-Phenoxyethanol<br>b) Phenylpropanol<br>   1,2-Octanediol<br>   1,3-Propanediol | a) 0.40<br>b) 0.10 | Passed | clear/almost clear |

TABLE 1-continued

| Example | Polymer in aqueous polymer solution | Preservative mixture | Concentration of the individual components in the polymer solution (% by weight) | Germ loading test | Appearance of the stabilized solution |
|---|---|---|---|---|---|
| 3 | Luviset Clear * | a) Phenoxyethanol<br>c) 1,2-Pentanediol<br>1,2-Octanediol<br>1,2-Decanediol | a) 0.1<br>c) 0.45 | Passed | Almost clear, very slightly cloudy |
| 4 | Luviset Clear * | a) Phenoxyethanol<br>c) 1,2-Pentanediol<br>1,2-Octanediol<br>1,2-Decanediol) | a) 0.45<br>c) 0.25 | Passed | Almost clear |
| 5 | Luvigel Star ** | a) 2-Phenoyxethanol<br>b) Phenylpropanol<br>1,2-Octanediol<br>1,3-Propanediol | a) 0.35<br>b) 0.35 | Passed | Clear |
| 6 | Luvigel Star ** | a) Phenoxyethanol<br>c) 1,2-Pentanediol<br>1,2-Octanediol<br>1,2-Decanediol | a) 0.2<br>c) 0.6 | Passed | Clear |
| 7 | Luvigel Star ** | a) Phenoxyethanol<br>c) 1,2-Pentanediol<br>1,2-Octanediol<br>1,2-Decanediol | a) 0.55<br>c) 0.25 | Passed | Clear |
| 8 | Luvigel Star ** | a) 2-Phenoyxethanol<br>b) Phenylpropanol<br>1,2-Octanediol<br>1,3-Propanediol | a) 0.25<br>b) 0.55 | Passed | Clear |
| 9 | Luviquat Hold*** | a) Phenoxyethanol<br>b) Phenylpropanol<br>1,2-Octanediol<br>1,3-Propanediol | a) 0.10<br>b) 0.30 | Passed | Clear |
| 10 | Luviquat Hold*** | a) Phenoxyethanol<br>b) Phenylpropanol<br>1,2-Octanediol<br>1,3-Propanediol | a) 0.40<br>b) 0.10 | Passed | Clear |
| 11 | Luviquat Hold*** | a) Phenoxyethanol<br>c) 1,2-Pentanediol<br>1,2-Octanediol<br>1,2-Decanediol | a) 0.1<br>c) 0.45 | Passed | Almost clear, very slightly cloudy |
| 12 | Luviquat Hold*** | a) Phenoxyethanol<br>c) 1,2-Pentanediol<br>1,2-Octanediol<br>1,2-Decanediol | a) 0.45<br>c) 0.25 | Passed | Almost clear |
| 13 | Luviskol K85/ K90**** | a) Phenoxyethanol<br>b) Phenylpropanol<br>1,2-Octanediol<br>1,3-Propanediol | a) 0.15<br>b) 0.35 | Passed | Clear |
| 14 | Luviskol K85/ K90**** | a) Phenoxyethanol<br>b) Phenylpropanol<br>1,2-Octanediol<br>1,3-Propanediol | a) 0.45<br>b) 0.25 | Passed | Clear |
| 15 | Luviskol K85/ K90**** | a) Phenoxyethanol<br>c) 1,2-Pentanediol<br>1,2-Octanediol<br>1,2-Decanediol | a) 0.50<br>c) 0.15 | Passed | Clear/almost clear |
| 16 | Luviskol K 85**** | d) Phenoxyethanol Ethylhexylglyceryl<br>e) Ethanol | d) 0.75<br>e) 0.1 | Passed | Clear |
| 17 | Luviskol K 85**** | d) Phenoxyethanol Ethylhexylglyceryl<br>e) Ethanol | d) 1.00<br>e) 0.1 | Passed | Clear |
| 18 | Luviskol K90***** | d) Phenoxyethanol Ethylhexylglyceryl<br>e) Isopropanol | d) 1.10<br>e) 0.25 | passed | Clear |

\* = Copolymer of vinylpyrrolidone, methacrylamide and vinylimidazole 20% strength aqueous solution
\*\* = Polyurethane -39, 20% strength aqueous solution
\*\*\*= Polyquaternium -46, 20% strength aqueous solution
\*\*\*\*= Polyvinylpyrrolidone, 20% strength aqueous solution Furthermore, comparative experiments with polymer solutions according to comparative examples 1 to 14 were carried out, which comprise either only the phenoxyethanol a), ethanol e) or isopropanol e) on its own or the preservative mixtures b) and c) as stabilizer(s). Compared to the corresponding examples according to the invention, up to more than 10-fold the amount of preservative was used. In this regard, reference is made to table 2 below.

TABLE 2

| Comparative example | Polymer in aqueous polymer solution | Preservative or preservative mixture | Concentration of the individual components in the polymer solution (% by weight) | Germ loading test | Appearance of the stabilized solution |
|---|---|---|---|---|---|
| 1 | Luviset Clear * | c) 2-Phenoxyethanol | c) 1.15 | Not passed | Very slightly cloudy |
| 2 | Luviset Clear * | b) Phenylpropanol 1,2-Octanediol 1,3-Propanediol | b) 0.65 | Not passed | Slightly cloudy |
| 3 | Luviset Clear * | c) 1,2-Pentanediol 1,2-Octanediol 1,2-Decanediol | c) 0.75 | Not passed | cloudy/phase separation |
| 4 | Luvigel Star ** | b) 2-Phenoyxethanol | c) 1.50 | Not passed | Almost clear |
| 5 | Luvigel Star ** | d) Phenylpropanol 1,2-Octanediol 1,3-Propanediol | c) 0.95 | Not passed | Almost clear |
| 6 | Luvigel Star ** | c) 1,2-Pentanediol 1,2-Octanediol 1,2-Decanediol | d) 1.25 | Not passed | Minimal cloudy |
| 7 | Luviquat Hold*** | c) Phenoxyethanol | c) 1.15 | Not passed | Almost clear/very slightly cloudy |
| 8 | Luviquat Hold*** | d) Phenylpropanol 1,2-Octanediol 1,3-Propanediol | b) 0.6 | Not passed | Almost clear/very slightly cloudy |
| 9 | Luviquat Hold*** | c) 1,2-Pentanediol 1,2-Octanediol 1,2-Decanediol | c) 0.75 | Not passed | Cloudy/phase separation |
| 10 | Luviskol K85**** | d) Phenylpropanol 1,2-Octanediol 1,3-Propanediol | b) 0.65 | Not passed | Slightly cloudy |
| 11 | Luviskol K90***** | c) Phenoxyethanol | d) 1.25 | Not passed | Almost clear |
| 12 | Luviskol K90***** | c) 1,2-Pentanediol 1,2-Octanediol 1,2-Decanediol | c) 0.65 | Not passed | Cloudy |
| 13 | Luviskol K90***** | e) Ethanol | e) 3.00 | Not passed | Almost clear |
| 14 | Luviskol K90***** | d) Phenoxyethanol Ethylhexylglyceryl | d) 1.25 | Not passed | Almost clear |

\* = Copolymer of vinylpyrrolidone, methacrylamide and vinylimidazole 20% strength aqueous solution
\*\* = Polyurethane -39, 20% strength aqueous solution
\*\*\*= Polyquaternium -46, 20% strength aqueous solution
\*\*\*\*= Polyvinylpyrrolidone, 20% strength aqueous solution
\*\*\*\*\*= Polyvinylpyrrolidone, 20% strength aqueous solution As can be seen by reference to comparative examples 1 to 14, the polymer solutions stabilized with phenoxyethanol, ethanol or isopropanol on its own or the preservative mixtures b) and c) have overall not passed the germ loading test. After 7, 14 and 28 days, freedom from germs was found with regard to the tested strains *Pseudomonas aeruginosa* (ATCC 9027), *Staphylococcus aureus* (ATCC 6638) and *Candida albicans* (ATCC 10231). However a colonization with *Aspergillus brasiliensis* (ATCC 16404) was established. Moreover, the aqueous comparison polymer solutions exhibited a cloudy, yellowish coloration, and they are unacceptably odor-intensive. Moreover, the preservative mixtures b) and c) are extremely expensive and therefore not very economical compared to the boosting preservative mixtures according to the invention.

The invention claimed is:

1. An aqueous 2-methylisothiazolin-3-one-free polymer solution stabilized with a preservative mixture of phenoxyethanol and at least one further alcohol,
wherein the polymer is selected from the group consisting of vinyllactam polymers, polyurethanes, and mixtures thereof, and wherein the preservative mixture comprises the following constituents as active biocidal ingredients:
from 25 to 50% by weight of a mixture composed of 50% 3-phenylpropanol, 25% 1,3-propanediol, and 25% 1,2-octanediol, and
from 50 to 75% by weight of phenoxyethanol, and the preservative mixture is used in an amount of from 0.10 to 1.40% by weight in the aqueous polymer solution,
or the preservative mixture comprises the following constituents as active biocidal ingredients:
from 20 to 57% by weight of a mixture composed of 50% 1,2-pentanediol, 30% 1,2-octanediol, and 20% 1,2-decanediol, and from 43 to 80% by weight of phenoxyethanol, and the preservative mixture is used in an amount of from 0.20 to 1.40% by weight in the aqueous polymer solution.

2. The polymer solution according to claim 1, wherein the vinyllactam polymer is a homopolymer or a copolymer of N-vinylpyrrolidone, 3-methyl-N-vinylpyrrolidone, 4-methyl-N-vinylpyrrolidone, 5-methyl-N-vinylpyrrolidone, N-vinylpiperidone, or N-vinylcaprolactam.

3. A cosmetic preparation or a product for the home care sector comprising the aqueous polymer solution according to claim 1.

4. The preparation or product according to claim 3 comprising skin care and hair care compositions.

5. A hairstyling product or a decorative cosmetics product or a hair and body cleaning product comprising the aqueous polymer solution according to claim 1.

6. The polymer solution according to claim 1 wherein the preservative mixture comprises
   from 25 to 50% by weight of a mixture composed of 50% 3-phenylpropanol, 25% 1,3-propanediol and 25% 1,2-octanediol, and
   from 50 to 75% by weight of phenoxyethanol, and
   the preservative mixture is used in an amount of from 0.10 to 0.65% by weight in the aqueous polymer solution.

7. The polymer solution according to claim 6 wherein the preservative mixture is used in an amount of from 0.10 to 0.40% by weight of the aqueous polymer solution.

8. The polymer solution according to claim 1 wherein the preservative mixture comprises from 20 to 57% by weight of a mixture composed of 50% 1,2-pentanediol, 30% 1,2-octanediol, and 20% 1,2-decanediol, and from 43 to 80% by weight of phenoxyethanol, and
   the preservative mixture is used in an the amount of from 0.20 to 0.80% by weight in the aqueous polymer solution.

9. The polymer solution according to claim 8 wherein the preservative mixture is used in an amount from 0.40 to 0.60% by weight in the aqueous polymer solution.

* * * * *